United States Patent [19]

Fies et al.

[11] Patent Number: 5,616,679
[45] Date of Patent: Apr. 1, 1997

[54] POLYALKYLENE GLYCOL

[75] Inventors: Matthias Fies, Krefeld; Roland Grützmacher, Wüfrath; Alfred Westfechtel, Hilden, all of Germany

[73] Assignee: Henkel Kommanditgesellschaft auf Aktien, Duesseldorf, Germany

[21] Appl. No.: 549,776

[22] PCT Filed: May 13, 1994

[86] PCT No.: PCT/EP94/01553

§ 371 Date: Nov. 14, 1995

§ 102(e) Date: Nov. 14, 1995

[87] PCT Pub. No.: WO94/26804

PCT Pub. Date: Nov. 24, 1994

[30] Foreign Application Priority Data

May 14, 1993 [DE] Germany .......................... 43 16 245.2

[51] Int. Cl.⁶ .................................................. C08G 18/48
[52] U.S. Cl. .................. 528/76; 528/295.3; 528/301; 252/182.27; 568/616; 568/619; 568/698
[58] Field of Search ................. 528/76, 295.3, 528/301; 252/182.27; 568/616, 619, 698

[56] References Cited

U.S. PATENT DOCUMENTS 3,188,353  6/1965  Holtschmidt ..................... 260/615
3,296,317  1/1967  Stein et al. ..................... 260/635

FOREIGN PATENT DOCUMENTS

| 1198348 | 3/1966 | Germany . |
| 1225795 | 9/1966 | Germany . |
| 1768313 | 4/1971 | Germany . |
| 4215648 | 11/1993 | Germany . |
| 4308100 | 9/1994 | Germany . |
| WO9113918 | 9/1991 | WIPO . |

*Primary Examiner*—Rachel Gorr
*Attorney, Agent, or Firm*—Ernest G. Szoke; Wayne C. Jaeschke; John Daniel Wood

[57] ABSTRACT

A polyalkylene glycol having the general formula:

$$HO-[R-O-]_nH$$

in which n has a value of at least 2 and R is an alkylene radical containing at least 20 carbon atoms is provided. Preferred polyalkylene glycols have an alkylene radical which is a branched alkylene radical containing at least 10 carbon atoms in the main chain and a degree of polymerization such that n is from 4 to 7. The polyalkylene glycol is prepared by the acid-catalyzed polycondensation of a monomeric alkylene glycol at elevated temperature.

33 Claims, No Drawings

POLYALKYLENE GLYCOL

The present application was filed under the provisions of 35 USC 371 as the U.S. National Phase of PCT/EP94/01553 filed May 13, 1994, and published as WO94/26804 Nov. 24, 1994.

BACKGROUND OF THE INVENTION

This invention relates to polyalkylene glycol, to its production and to its use.

DISCUSSION OF RELATED ART

"Polyalkylene glycols" are understood to be predominantly linear polyethers corresponding to the following general formula:

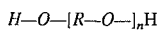

$$H{-}O{-}[R{-}O{-}]_nH$$

in which the hydroxyl groups are terminally positioned and the alkylene group R is a difunctional radical which contains 2 H atoms less than the corresponding alkane compound at two different C atoms. Known polyalkylene glycols are, for example, polyethylene glycol ($R=CH_2CH_2$), polypropylene glycol ($R=CH_2{-}CH_2(CH_2)$) or polytetramethylene glycol ($R=CH_2CH_2CH_2CH_2$). They are generally prepared by polyaddition of the corresponding cyclic ethers onto water or dihydric alcohols. The known polyalkylene glycols are liquid, wax-like or solid products according to their molecular weight. They are widely used. Above all, they are used as diol component in the production of polyurethanes and polyesters. They provide above all for an improvement in hydrolytic stability by comparison with the corresponding polyester diols. In addition, they are used for the production of nonionic emulsifiers, surfactants or wetting agents and as solvents, plasticizers or solubilizers.

Low molecular weight diols, for example ethylene glycol, hexanediol, decane-1,10-diol, 1,4-cyclohexane dimethanol or dimer diol, are used for similar purposes.

The dimer diol has been known for some time. Thus, its production by dimerization of unsaturated fatty alcohols with basic alkaline earth metal compounds at more than 280° C. was described, for example, about 30 years ago in DE 11 98 348. It may also be prepared by hydrogenation of dimeric fatty acids and/or esters thereof in accordance with DE-B-17 68 313. Suitable adducts are dimerization products of monounsaturated and/or polyunsaturated fatty acids and/or esters thereof, for example dimerization products of oleic acid, linoleic acid, linolenic acid, palmitoleic acid, elaidic acid and/or erucic acid and/or esters thereof. Particularly preferred adducts are dimerization products of monounsaturated or polyunsaturated fatty acid mixtures of the type obtained in the hydrolysis of natural fats and/or oils, for example olive oil, sunflower oil, soybean oil, cottonseed oil/coriander oil and/or tall oil. Depending upon the reaction conditions selected for the dimerizations known per se, varying amounts of oligomeric fatty acids and/or residual quantities of monomeric fatty acids or esters thereof may be present in addition to dimer fatty acids. If the dimerized fatty acids or fatty acid esters contain relatively large quantities of monomeric fatty acids or fatty acid esters, it may be advisable to remove them by distillation, preferably as fatty acid esters of lower $C_{1-4}$ alcohols, after or before hydrogenation to the dimer diols. The hydrogenations of the dimerized fatty acids or esters thereof may be carried out in accordance with DE-B-17 68 313 in the presence of copper- and/or zinc- containing catalysts in typical continuous pressure hydrogenation reactors with gas circulation. Under these conditions, not only are the carboxyl groups of the fatty acids hydrogenated to hydroxyl groups, double bonds still present in the dimerized fatty acids or their esters may also be partly or completely hydrogenated. However, the hydrogenation may also be carried out in such a way that the double bonds remain fully intact during the hydrogenation reaction. In this case, unsaturated dimer diols are formed, optionally in admixture with trimer triols and residual monomers. However, the hydrogenation is preferably carried out in such a way that the double bonds are at least partly or completely hydrogenated. Another method of preparing completely saturated dimer diols is to convert saturated dimer fatty acids into the corresponding saturated dimer diols by hydrogenation. Another method of preducing dimer diols is to dimerize unsaturated alcohols in the presence of silica/alumina catalysts and basic alkali metal compounds in accordance with International patent application WO 91/13918. Suitable unsaturated alcohols are monounsaturated and/or polyunsaturated fatty alcohols, such as palmitoleyl, oleyl, elaidyl, linolyl, linolenyl and erucyl alcohol. This process gives unsaturated dimer diols of which the double bonds may then be partly or completely hydrogenated.

Dimer diols which have been produced from fatty acids or esters thereof or fatty alcohols containing 18 carbon atoms are used on an industrial scale, irrespective of the described processes for the production of the dimer diols. Dimer diols containing 36 carbon atoms are formed in this way. As already mentioned, dimer diols produced by the industrial processes mentioned above always contain varying amounts of trimer triols and residual monomers. In general, the percentage content of dimer diols is more than 70% by weight, the remainder being trimer triols and monomer alcohols. However, there are also purer dimer diols containing more than 90% by weight of dimer diol and, more particularly, more than 90 to 99% by weight of dimer diol. Of these dimer diols, those of which the double bond is at least partly or completely hydrogenated are preferably used for subsequent reactions.

It is also known that the dimer diol can be used as a polyol for the production of polyurethane coatings by reaction with diisocyanates. Thus, DE 12 25 795 describes polyurethane paints of dimeric and/or trimeric fatty alcohols containing an average of 36 or 54 carbon atoms. The fatty alcohols mentioned are preferably used as sole hydroxyl compounds. However, small quantities of other known hydroxyl compounds suitable for the production of polyurethane paints may also be used. The polyurethane paints are distinguished inter alia by high resistance to hydrolyzing chemicals, more particularly to solutions of substances showing an alkaline reaction. Polyester polyols were used for comparison.

Other applications for the production of polyurethanes are described in DE 42 15 648 and DE 43 08 100.

The known diols for the production of polyurethanes and polyesters are either solid or hydrophilic compounds or have a high hydroxyl value. This is a disadvantage in a number of cases. Thus, the high consumption of isocyanate or acid components is a disadvantage in the processing of diols having a high hydroxyl value. The processing of solid compounds is often difficult, for example in regard to homogenization of the reaction mixture. In many applications, the hydrophilic diol component adversely affects the properties of the end product, for example in regard to its behavior towards water (hydrolysis stability, wetting properties).

Accordingly, there is a need for a liquid hydrophobic diol having a low hydroxyl value.

SUMMARY OF THE INVENTION

The solution provided by the present invention is defined in the claims and lies in the provision of a polyalkylene glycol corresponding to the general formula:

$$HO-[R-O-]_nH$$

in which n has a value of 2 or more and R is an alkylene radical containing 20 or more carbon atoms.

DETAILED DESCRIPTION OF THE INVENTION

The alkylene radical is a difunctional radical which contains 2 H atoms less at two different carbon atoms than the corresponding branched, unbranched or cyclic alkane containing in particular 30 or more carbon atoms. It is preferably branched and contains at least 10 carbon atoms between the radical sites. The alkylene radical is derived from primary alcohols. Accordingly, the OH groups of the polyalkylene glycols are terminal and primary. Specific examples of the alkylene radicals are those derived from the following low molecular weight diols: $C_{36}$ dimer diol, $C_{44}$ dimer diol.

The degree of polymerization n is understood to be the number of recurring alkylene radicals. In the case of molecularly non-uniform products, it is understood to be the average degree of polymerization (DP). The degree of polymerization of uniform polyalkylene glycols is 2 or more, more particulary 4 to 7. The average degree of polymerization is more than 1.0 and, more particularly, is between 1.5 and 5. Accordingly, the polyalkylene glycols according to the invention are oligomers of which the individual constituents can be separated, for example, by gel chromatography. The degree of polymerization (DP) may be regulated through the amount of water to be removed.

The polyalkylene glycols according to the invention have a hydroxyl value (OHV) of less than 175 and, more particularly, between 10 and 100. The OH value indicates the number of milligrams of KOH which is equivalent to the quantity of acetic acid bound by 1 g of substance during the acetylation reaction.

The polyalkylene glycols according to the invention are liquid at room temperature (20° C.), i.e. they have a viscosity at 25° C. of >3,000 mPa.s and, more particularly, in the range from 3,800 to 12,000 mPa.s.

The polyalkylene glycols according to the invention are hydrophobic, i.e. they are substantially insoluble in water at 20° C., preferably less than 1 mg and, more preferably, less than 0.1 mg dissolving in 100 ml of water.

The polyalkylene glycols according to the invention may be prepared by acid-catalyzed polycondensation of suitable low molecular weight alkylene glycols at elevated temperature. Suitable catalysts are sulfuric acid, hydrochloric acid, organic sulfonic acids (such as benzene, toluene or naphthalene sulfonic acid and methionic acid=methane disulfonic acid), also phosphoric acid, perchloric acid, boron trifluoride either individually or in conjunction with an aromatic sulfonic acid and also acidic or readily hydrolyzable or dissociating salts (such as alkali metal hydrogen sulfate, zinc chloride, quinoline hydrochloride, etc.). Among these, sulfuric acid and methane sulfonic acid play by far the most important role. The acid is used in a quantity of 0.5 to 30% by weight and, more particularly, in a quantity of 5 to 15% by weight, based on the diol used.

The condensation temperature is at least 150° C. and, more particularly, is in the range from 200° to 250° C.

To produce the polyethers according to the invention, the acid is generally added to the diol and the reaction mixture is subsequently heated to the reaction temperature until the theoretically calculated quantity of water is obtained in the water separator. This generally takes 2 to 20 hours and preferably 6 to 12 hours. The yield is quantitative. The reaction product is preferably not purified. Accordingly, the conversion is preferably 100%. The reaction product is yellow and clear.

The polyalkylene glycols according to the invention are particularly suitable for use as a component in the production of plastics by polycondensation, polyaddition or polymerization, more particularly for the production of polyesters and polyurethanes, above all thermoplastic polyurethanes with a low glass temperature. Other plastics include polycondensation plastics.

These plastics are particularly suitable for use as a basic material for sealing compounds, adhesives and coating materials, more especially for paints. They are distinguished by a hydrophobic effect, for example by minimal moisture absorption and minimal wetting with water. The plastics produced with the polyalkylenes according to the invention therefore show particular stability to hydrolysis both towards acids and towards bases.

In addition, the polyalkylene glycols according to the invention are suitable for use as lubricating oils, plasticizers and textile auxiliaries.

The invention is illustrated by the following Examples.

EXAMPLES

Example 1

Polyalkylene Glycol with an OHV of 28

678 g (1.3 moles) of dimer diol (Sovermol POL 900: OHV 208, SV 1.8, IV 42, AV 0.2) and 6.8 g of methane sulfonic acid were heated for 10 hours to 200° C. on a water separator. The end product is a yellow clear polyol. The yield is quantitative. Viscosity=11,900 mPas (Brookfield, 25° C.). OHV 28, AV 1.8, IV 37. GPC: 10% degree of polymerization 4, 10% degree of polymerization 5, 20% degree of polymerization 6, 40% degree of polymerization 7.

Example 2

Polyalkylene Glycol with an OH Value of 39

1000 g (1.9 moles) of dimer diol (Sovermol POL 900, OHV 208, SV 1.8, IV 42, AV 0.2) and 10.0 g of methane sulfonic acid were heated for 8 hours to 200° C. on a water separator. The end product is a yellow clear polyol. The yield is quantitative. OHV 39, AV 2.7.

Example 3

Polyalkylene Glycol with an OH Value of 15.5

1000 g (3.7 moles) of dimer diol (Sovermol POL 900: OHV 208, SV 1.8, IV 42, AV 0.2) and 10.0 g of methane sulfonic acid were heated for 8 hours to 240° C. on a water separator. The end product is a yellow clear polyol. The yield is quantitative. OHV 15.5, AV 1.5. GPC: 7% degree of polymerization 4, 7% degree of polymerization 5, 25% degree of polymerization 6, 45% degree of polymerization 7.

The abbreviations have the following meanings:
OHV=hydroxyl value. This indicates the number of milligrams of potassium hydroxide which are equivalent to the quantity of acetic acid bound by 1 g of substance during the acetylation reaction. The sample is boiled with acetic anhydride/pyridine and the acid formed is filtered with KOH solution.

SV=saponification value. This is the characteristic measure of the concentration of esters present in the diol.

IV=iodine value. The iodine value is a measure of the degree of unsaturation of the diols. The double bonds present in the molecule are titrated with elemental bromine and the consumption is converted to iodine.

AV=acid value. The acid value is a measure of the content of free organic acids in the diol. It indicates the number of milligrams of KOH which are used to neutralize 1 g of the diols.

GPC=gel permeation chromatography. The oligomers are separated from one another as follows: PL - Gel system: PL-gel preliminary column, 2×100 A, 2×50 A, mobile solvent: THF 1 ml/min., 40° C.

Viscosity: Brookfield at 25° C., Model DV-II, spindle 21.

We claim:

1. A polyalkylene glycol having the general formula:

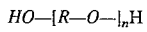

$$HO-[R-O-]_nH$$

in which n has a value of at least 2 and R is an alkylene radical containing at least 20 carbon atoms.

2. A polyalkylene glycol as claimed in claim 1 wherein said alkylene radical is a branched alkylene radical containing at least 10 carbon atoms in the main chain.

3. A polyalkylene glycol as claimed in claim 1 wherein n is from 4 to 7.

4. A polyalkylene glycol as claimed in claim 1 wherein said alkylene radical has at least 30 carbon atoms.

5. A polyalkylene glycol as claimed in claim 1 wherein alkylene radical has 36 carbon atoms.

6. A polyalkylene glycol as claimed in claim 1 wherein alkylene radical has 44 carbon atoms.

7. A polyalkylene glycol as claimed in claim 1 wherein said polyalkylene glycol has a hydroxyl value of less than 175.

8. A polyalkylene glycol as claimed in claim 1 wherein said polyalkylene glycol has a hydroxyl value of 10 to 100.

9. A polyalkylene glycol as claimed in claim 1 wherein said polyalkylene glycol is liquid at 20° C. and has a viscosity at 25° C. of greater than 3,000 mPa.s.

10. A polyalkylene glycol as claimed in claim 9 wherein said viscosity is from 3,800 to 12,000 mPa.s.

11. A polyalkylene glycol as claimed in claim 1 wherein said polyalkylene glycol is essentially insoluble in water at 20° C.

12. A polyalkylene glycol as claimed in claim 1 wherein said polyalkylene glycol has a solubility in water of less than 1 mg per 100 ml of water.

13. A polyalkylene glycol as claimed in claim 1 wherein said polyalkylene glycol has a solubility in water of less than 0.1 mg per 100 ml of water.

14. A polyalkylene glycol having the general formula:

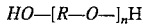

$$HO-[R-O-]_nH$$

in which n has a value of 4 to 7 and R is an alkylene radical containing at least 30 carbon atoms.

15. A process for the production of a polyalkylene glycol having the general formula:

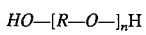

$$HO-[R-O-]_nH$$

in which n has a value of at least 2 and R is an alkylene radical containing 20 or more carbon atoms, said process comprising condensing a monomeric alkylene glycol corresponding to the above formula wherein n is one, at elevated temperature in the presence of an acid catalyst.

16. A process as claimed in claim 15 wherein said elevated temperature is at least 150° C.

17. A process as claimed in claim 15 wherein said elevated temperature is from 200° C. to 250° C.

18. A process as claimed in claim 15 wherein said acid catalyst is selected from the group consisting of sulfuric acid, hydrochloric acid, methanesulfonic acid, benzenesulfonic acid, toluenesulfonic acid, naphthalenesulfonic acid, methionic acid, phosphoric acid, perchloric acid, and boron trifluoride.

19. A process as claimed in claim 15 wherein said acid catalyst is selected from the group consisting of sulfuric acid and methanesulfonic acid.

20. A process as claimed in claim 15 wherein said acid catalyst is present in an amount of from 0.5% to 30% by weight of said alkylene glycol.

21. A process as claimed in claim 15 wherein said acid catalyst is present in an amount of from 5% to 15% by weight of said alkylene glycol.

22. A process as claimed in claim 15 wherein the conversion of said alkylene glycol to said polyalkylene glycol is essentially 100%.

23. A process for the production of a polyalkylene glycol having the general formula:

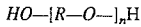

$$HO-[R-O-]_nH$$

in which n has a value of at least 2 and R is an alkylene radical containing 20 or more carbon atoms, said process comprising condensing a monomeric alkylene glycol corresponding to the above formula wherein n is one, at a temperature of 200° C. to 250° C. in the presence of an acid catalyst selected from the group consisting of sulfuric acid and methanesulfonic acid in a quantity of from 5% to 15% by weight of said alkylene glycol.

24. In a method for the production of a polyester, the improvement comprising using as a diol, a polyalkylene glycol as claimed in claim 1.

25. In a method of bonding, sealing or coating, the improvement comprising using a polyester as claimed in claim 24.

26. In a method for the production of a polyurethane, the improvement comprising using as a diol, a polyalkylene glycol as claimed in claim 1.

27. A method as claimed in claim 26 wherein said polyurethane is a thermoplastic polyurethane.

28. In a method of bonding, sealing or coating, the improvement comprising using a polyurethane as claimed in claim 26.

29. In a method for the production of a polyester, the improvement comprising using as a diol, a polyalkylene glycol as claimed in claim 14.

30. In a method of bonding, sealing or coating, the improvement comprising using a polyester as claimed in claim 29.

31. In a method for the production of a polyurethane, the improvement comprising using as a diol, a polyalkyene glycol as claimed in claim 14.

32. A method as claimed in claim 31 wherein said polyurethane is a thermoplastic polyurethane.

33. In a method of bonding, sealing or coating, the improvement comprising using a polyurethane as claimed in claim 31.

* * * * *